(12) United States Patent
Avitall

(10) Patent No.: US 10,285,749 B2
(45) Date of Patent: May 14, 2019

(54) DETERMINATION OF PULMONARY VEIN AND OTHER VASCULAR OCCLUSION USING TEMPERATURE PROFILE FOLLOWING COLD SALINE INJECTION

(71) Applicant: Medtronic CryoCath LP, Toronto (CA)

(72) Inventor: Boaz Avitall, Chicago, IL (US)

(73) Assignee: Medtronic Cryocath LP, Toronto, Ontario (CA)

( * ) Notice: Subject to any disclaimer, the term of this patent is extended or adjusted under 35 U.S.C. 154(b) by 1055 days.

(21) Appl. No.: 14/689,174

(22) Filed: Apr. 17, 2015

(65) Prior Publication Data

US 2016/0157914 A1    Jun. 9, 2016

Related U.S. Application Data

(60) Provisional application No. 62/088,267, filed on Dec. 5, 2014.

(51) Int. Cl.
*A61B 18/02* (2006.01)
*A61B 6/00* (2006.01)
*A61B 18/00* (2006.01)

(52) U.S. Cl.
CPC .......... *A61B 18/0218* (2013.01); *A61B 6/481* (2013.01); *A61B 6/485* (2013.01);
(Continued)

(58) Field of Classification Search
CPC ......... A61B 6/481; A61B 6/485; A61B 6/487; A61B 6/504; A61B 18/02; A61B 18/0218;
(Continued)

(56) References Cited

U.S. PATENT DOCUMENTS 4,682,596 A    7/1987 Bales et al.
5,014,715 A    5/1991 Chapolini
(Continued)

FOREIGN PATENT DOCUMENTS

CA    2903280 A1    9/2014
EP    1025805 A1    9/2000
(Continued)

OTHER PUBLICATIONS

Boaz Avitall, MD, PHD, Fhrs et al., The characteristics of distal balloon impedance and temperature changes during Cryo ablation: Can it guide the Cryo application?, Abstract, 2015 Heart Rhythm, May 13-16, 2015, Boston, MA. Oasis, The Online Abstract Submission System.

(Continued)

*Primary Examiner* — Michael J Carey
(74) *Attorney, Agent, or Firm* — Christopher & Weisberg, P.A.

(57) ABSTRACT

A method, system, and device for predicting lesion quality. Specifically, lesion quality may be predicted based on an assessment of pulmonary vein occlusion using saline injection and evaluation of temperature measurements recorded by a thermocouple located distal to the cryoballoon of the treatment device. The quality of the occlusion may be rated based on the time it takes the temperature recorded by the thermocouple to increase from approximately 2° C. to approximately 38° C., the rate of temperature change over a predetermined time period, and/or the rate of dissipation within the pulmonary vein of the saline with a volume of contrast medium. For example, the quality of the occlusion may be rated as being good, fair, or poor. This assessment may be quickly and easily communicated to an operator.

22 Claims, 6 Drawing Sheets

(52) U.S. Cl.
CPC .............. *A61B 6/504* (2013.01); *A61B 18/02* (2013.01); *A61B 6/487* (2013.01); *A61B 2018/0022* (2013.01); *A61B 2018/00285* (2013.01); *A61B 2018/00375* (2013.01); *A61B 2018/00577* (2013.01); *A61B 2018/00648* (2013.01); *A61B 2018/00738* (2013.01); *A61B 2018/00821* (2013.01); *A61B 2018/0212* (2013.01)

(58) Field of Classification Search
CPC .. A61B 2018/0022; A61B 2018/00285; A61B 2018/00375; A61B 2018/00577; A61B 2018/00648; A61B 2018/00738; A61B 2018/00821; A61B 2018/0212
USPC .......................................................... 606/21
See application file for complete search history.

(56) References Cited

U.S. PATENT DOCUMENTS

| | | | |
|---|---|---|---|
| 5,639,444 | A | 6/1997 | Klaveness |
| 7,951,088 | B2 | 5/2011 | Korotko et al. |
| 8,295,908 | B2 | 10/2012 | Carmeli et al. |
| 2002/0151880 | A1 | 10/2002 | Lafontaine |
| 2003/0158490 | A1 | 8/2003 | Krivitski et al. |
| 2003/0216661 | A1 | 11/2003 | Davies |
| 2007/0066975 | A1 | 3/2007 | Wong et al. |
| 2009/0182318 | A1 | 7/2009 | Abboud et al. |
| 2010/0041984 | A1 | 2/2010 | Shapland et al. |
| 2010/0130854 | A1 | 5/2010 | Shachar et al. |
| 2011/0144637 | A1 | 6/2011 | Pageard et al. |
| 2011/0152712 | A1 | 6/2011 | Cao et al. |
| 2012/0095461 | A1 | 4/2012 | Herscher et al. |
| 2014/0276709 | A1* | 9/2014 | Wittenberger ..... A61B 18/1492 606/23 |
| 2014/0330262 | A1 | 11/2014 | Jannicke et al. |
| 2015/0164570 | A1 | 6/2015 | Wittenberger et al. |

FOREIGN PATENT DOCUMENTS

| | | |
|---|---|---|
| WO | 9835611 A1 | 8/1998 |
| WO | 2008088579 A2 | 7/2008 |

OTHER PUBLICATIONS

Boaz Avitall, MD, PHD, Fhrs et al., Distal Cryo balloon temperature sensor to assess PV occlusion: Eliminating the need for contrast and fluoroscopy, Abstract, 2015 Heart Rhythm, May 13-16, 2015, Boston, MA. Oasis, The Online Abstract Submission System.

Supplementary European Search Report and Search Opinion dated Jun. 7, 2018, for corresponding European Application No. 15864380.9; consisting of 7-pages.

International Search Report and Written Opinion dated Jan. 7, 2016, for corresponding International Application No. PCT/CA2015/051250; International Filing Date: Dec. 1, 2015 consisting of 9-pages.

International Search Report and Written Opinion dated Mar. 2, 2016, for corresponding International Application No. PCT/CA2015/051272; International Filing Date: Dec. 4, 2015 consisting of 10-pages.

European Search Report and Written Opinion dated Aug. 6, 2018, for corresponding European Application No. EP15865807; consisting of 2-pages.

* cited by examiner

DETERMINATION OF PULMONARY VEIN AND OTHER VASCULAR OCCLUSION USING TEMPERATURE PROFILE FOLLOWING COLD SALINE INJECTION

CROSS-REFERENCE TO RELATED APPLICATION

This application is related to and claims priority to U.S. Provisional Patent Application Ser. No. 62/088,267, filed Dec. 5, 2014, entitled USE OF COLD SALINE TO REPLACE DYE IN DETERMINING CRYO BALLOON PV OCCLUSION, the entirety of which is incorporated herein by reference.

STATEMENT REGARDING FEDERALLY SPONSORED RESEARCH OR DEVELOPMENT n/a

FIELD OF THE INVENTION

The present Application relates to a method, system, and device for predicting lesion quality and other interventions requiring vascular occlusion. Specifically, lesion quality may be predicted based on an assessment of pulmonary vein occlusion using saline injection. This assessment may be quickly and easily communicated to an operator.

BACKGROUND OF THE INVENTION

Cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially.

Procedures such as pulmonary vein isolation (PVI) are commonly used to treat atrial fibrillation. This procedure generally involves the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium. If a cryoballoon is used as the treatment element of the cryogenic device, the balloon is typically inflated using a fluid coolant, enabling the balloon to create a circumferential lesion about the ostium and/or antrum of the PV to disrupt aberrant electrical signals exiting the PV.

The success of this procedure depends largely on the quality of the lesion(s) created during the procedure. Currently known methods for evaluating lesion quality may include monitoring the temperature within the cryoballoon, but this method can be inaccurate. The success of a PVI procedure also depends on whether the cryoballoon has completely occluded the PV. For example, a complete circumferential lesion is produced only when the cryoballoon has completely occluded the PV. Incomplete occlusion allows blood to flow from the PV being treated, past the cryoballoon, and into the left atrium of the heart. This flow of warm blood may prevent the cryoballoon from reaching temperatures low enough to create permanent lesions in the target tissue, or could leave gaps of non-ablated tissue at regions where blood leaks past the balloon. The creation of reversible lesions may not be sufficient to achieve electrical isolation and, as a result, atrial fibrillation may be likely to reoccur. Additionally, even if the PV is completely occluded, suboptimal operation of the cryoablation system may result in cryoballoon temperatures that are not low enough, or not applied for a sufficient amount of time, to create permanent lesions in the target tissue.

Current methods of assessing or monitoring PV occlusion include fluoroscopic imaging of radiopaque contrast medium injected from the device into the PV. If the device, such as a cryoballoon catheter, has not completely occluded the PV ostium, some of the contrast medium may flow from the PV into the left atrium. In that case, the device may be repositioned and more contrast medium injected into the PV. This method not only necessitates the use of an auxiliary imaging system, but it also exposes the patient to potentially large doses of contrast medium and radiation.

It is therefore desirable to provide a cryoablation method, system, and device that reduces a patient's exposure to radiation and contrast medium but still allows for real-time and accurate assessment of PV occlusion before a PV ablation procedure. It is also desirable to provide for a method, system, and device that allow for the communication of PV occlusion assessment to the operator quickly and easily.

SUMMARY OF THE INVENTION

A method, system, and device for predicting lesion quality. Specifically, lesion quality may be predicted based on an assessment of pulmonary vein occlusion using saline injection and evaluation of temperature measurements recorded by a thermocouple located distal to the cryoballoon of the treatment device. The quality of the occlusion may be rated based on the time it takes the temperature recorded by the thermocouple to increase from a temperature lower than body temperature such that a temperature gradient is created, for example, approximately 2° C. to approximately 38° C., the rate of temperature change over a predetermined time period, and/or the rate of dissipation within the pulmonary vein of the saline with a volume of contrast medium. For example, the quality of the occlusion may be rated as being good, fair, or poor. This assessment may be quickly and easily communicated to an operator.

A system for predicting lesion quality may include a treatment device and a console including: a source of cooled saline in fluid communication with the treatment device, the cooled saline being injected from the treatment device; an energy generator in electrical communication with the treatment device; and a processor programmed to receive temperature data recorded by the treatment device and to calculate a rate of temperature increase in the cooled saline, the processor being further programmed to determine a pulmonary vein occlusion status based at least in part on the rate of temperature increase, the lesion quality being based at least in part on the pulmonary vein occlusion status. The cooled saline may be injected from the treatment device at an injection temperature, the processor being programmed to calculate a rate of temperature increase from the injection temperature to a threshold temperature after injection of the cooled saline from the treatment device. For example, the threshold temperature may be approximately 38° C. and the injection temperature may be approximately 2° C. to approximately 3° C. A determination that the pulmonary vein is partially occluded may include at least one of assigning the occlusion by the processor a poor rating and assigning the occlusion a fair rating and a determination that the pulmonary vein is completely occluded includes assigning the occlusion by the processor a good rating. For example, occlusion may be assigned a good rating when the rate of temperature increase has a first value, occlusion may be assigned a fair rating when the rate of temperature increase has a second value, and occlusion may be assigned a poor rating when the rate of temperature increase has a third value, the first value being less than each of the second value and the third value. The treatment device may include a cryoballoon and electrode thermocouple located distal to the cryoballoon. The treatment device may further include an electrode proximate the thermocouple. The treatment device further may include a shaft having a central lumen and a distal opening, the shaft being at least partially disposed within the cryoballoon, the central lumen and distal opening being in fluid communication with the source of cooled saline. The cooled saline may include a volume of radiopaque contrast medium and the cooled saline with contrast medium may be injected into a pulmonary vein. The processor may be further programmed to calculate a dissipation time it takes the cooled saline with contrast medium to dissipate within the pulmonary vein, the processor being further programmed to determine the pulmonary vein occlusion status based at least in part on the dissipation time. For example, occlusion may be assigned a good rating when the dissipation time has a first value, occlusion may be assigned a fair rating when the dissipation time has a second value, and occlusion may be assigned a poor rating when the dissipation time has a third value, the first value being less than each of the second value and the third value. The processor may be further programmed to calculate a rate of temperature increase in the cooled saline from the injection temperature over a threshold period of time, such as between approximately 2 and approximately 15 seconds. Additionally or alternatively, the processor may be programmed to calculate a rate of temperature increase from the injection temperature to a temperature at two seconds after injection of the cooled saline from the treatment device.

A system for predicting lesion quality may include a treatment device including an occlusion element and a thermocouple distal to the occlusion element, the treatment device injecting cooled saline into a pulmonary vein at an injection temperature of between approximately 2° C. and approximately 3° C. and a processor in communication with and receiving temperature data from the thermocouple. The processor may be programmed to: calculate a rate of temperature increase from the cooled saline from the injection temperature to a temperature of approximately 38° C. over a predetermined period of time after the cooled saline is injected from the treatment device; and determine a pulmonary vein occlusion status based at least in part on the rate of temperature increase, the lesion quality being based at least in part on the pulmonary vein occlusion status. For example, an occlusion status of good may be assigned when the rate of temperature increase has a first value, an occlusion status of fair may be assigned when the rate of temperature increase has a second value, and an occlusion status of poor may be assigned when the rate of temperature increase has a third value, the first value being less than each of the second value and the third value. Further, the lesion quality may be assigned a value of good when the occlusion status is good.

A method for predicting lesion quality may include: injecting cooled saline from a medical device into a pulmonary vein, the medical device including an occlusion element at least partially occluding the pulmonary vein and a distal thermocouple positioned within the pulmonary vein; recording a temperature by the thermocouple within the pulmonary vein at each of a plurality of time intervals after injection of the cooled saline; comparing the temperatures recorded at each of the plurality of time intervals; assessing the quality of an occlusion of the pulmonary vein by the medical device based on the comparisons; and at least one of: repositioning the medical device when the quality of the occlusion is determined to be one of fair and poor; and ablating tissue surrounding the pulmonary vein with the occlusion element when the quality of the occlusion is determined to be good. Comparing the temperatures recorded at each of the plurality of time intervals may include determining a recovery time it takes the temperature within the pulmonary vein to increase from between approximately 2° C. and approximately 3° C. to approximately 38° C. For example, the quality of occlusion may be determined to be good when the recovery time is approximately 75.4±48.7 seconds.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
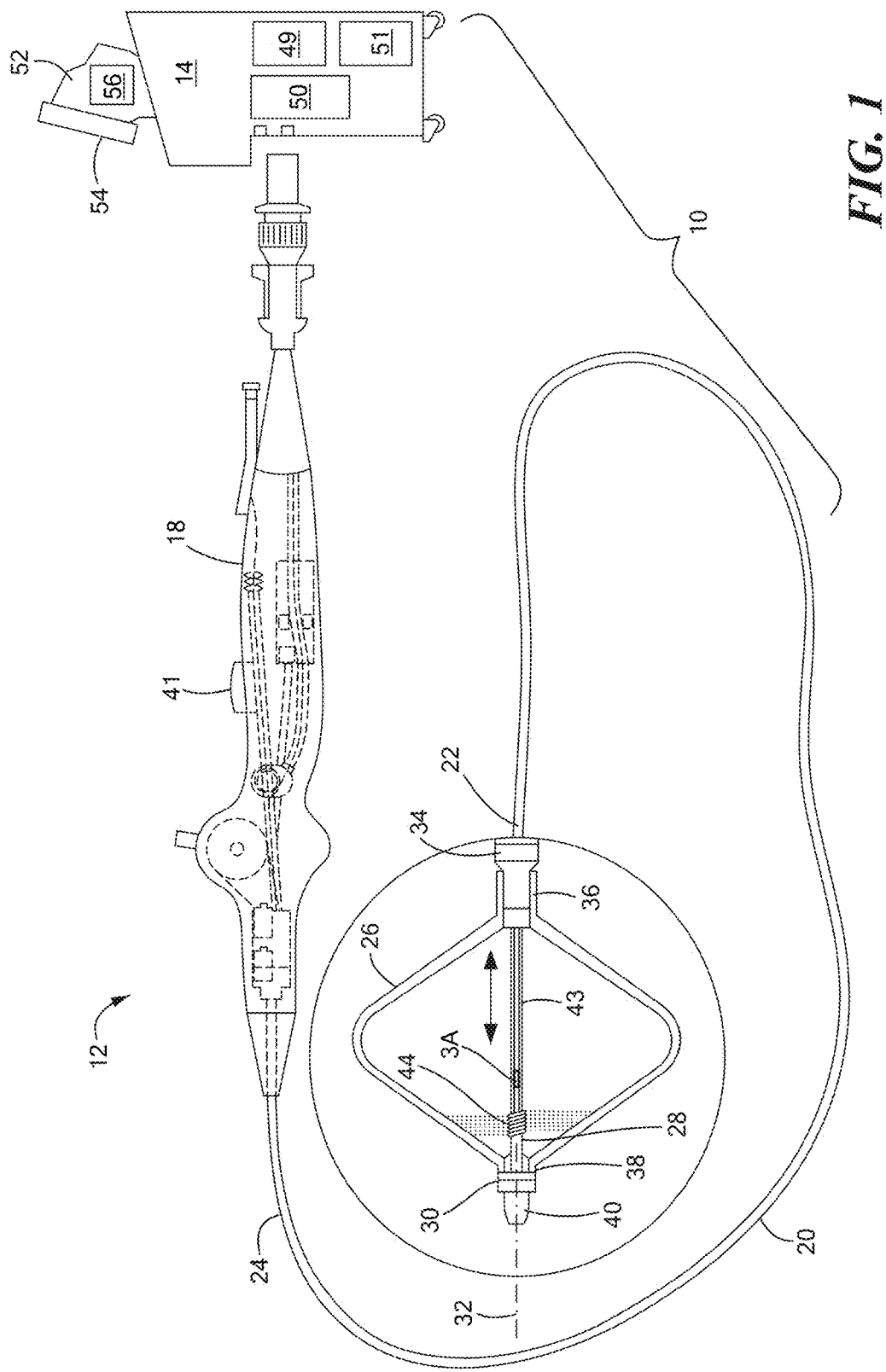
FIG. 1 shows an exemplary system for the assessment of pulmonary vein occlusion.
Figure 2:
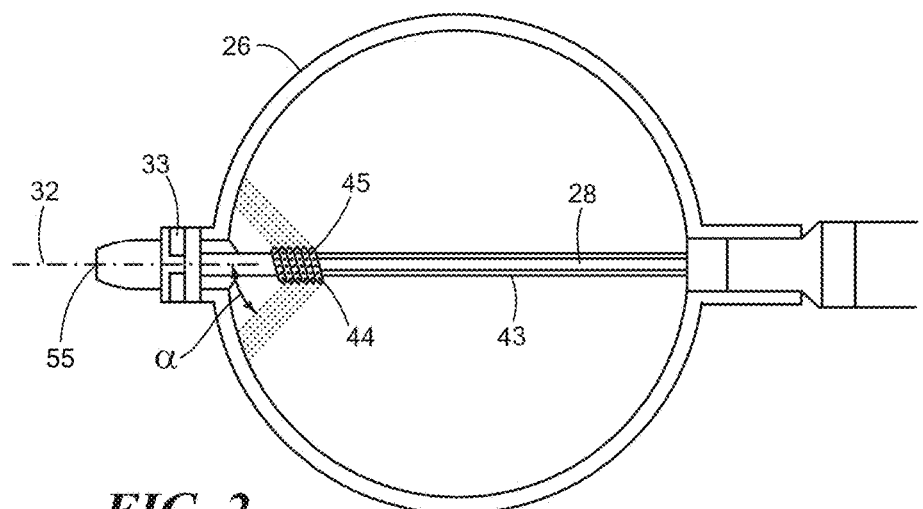
FIG. 2 shows a close-up view of a distal end of a medical device of the system in FIG. 1.

Referring now to FIGS. 1 and 2, an exemplary system for the assessment of pulmonary vein occlusion is shown. The system 10 may generally include a treatment device, such as a cryotreatment catheter 12, for thermally treating an area of tissue and a console 14 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof. The system 10 may also include a mapping catheter 16 for sensing and recording electrical signals from tissue (for example, cardiac tissue and/or tissue within a pulmonary vein).

Figure 3:
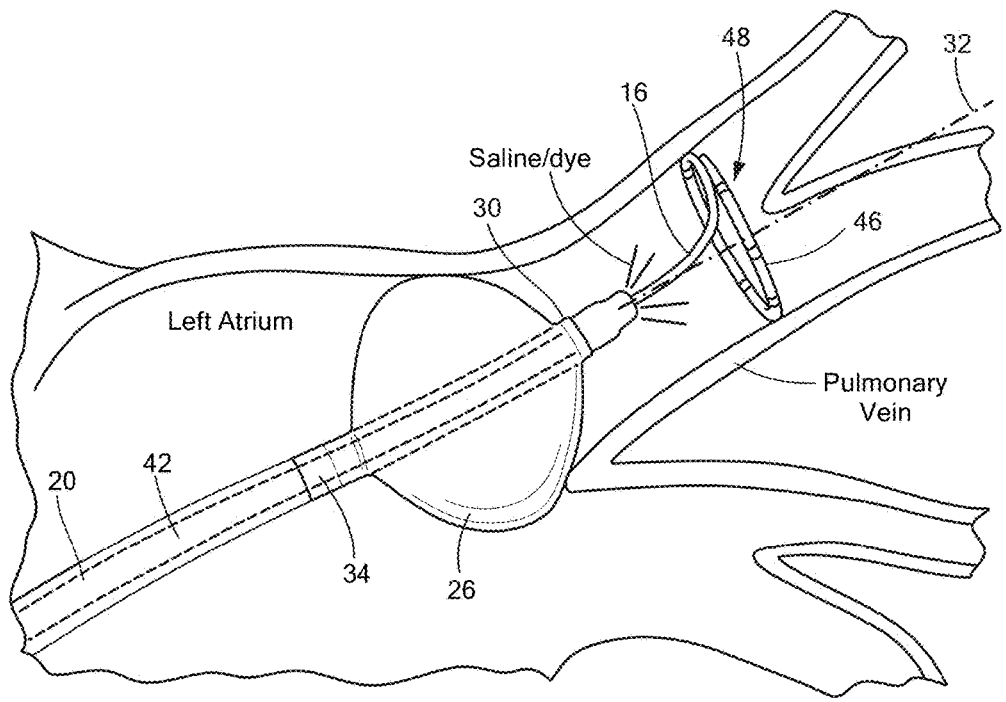
FIG. 3 shows an exemplary placement of the medical device of FIG. 2 proximate a pulmonary vein.

The cryotreatment catheter 12 may generally include a handle 18, an elongate body 20 having a distal portion 22 and a proximal portion 24, one or more treatment elements 26, a shaft 28, an electrode 30 distal to the one or more treatment elements 26, and a longitudinal axis 32. As a non-limiting example, the electrode 30 may be a 0.5 mm ring thermocouple electrode that functions as a thermocouple for recording temperature data and an electrode for delivering energy. For example, the cryotreatment catheter 12 may include one or more thermocouples 33 proximate (either distal to or proximal to) the electrode 30 (for example, as shown in FIG. 2). Optionally, the electrode 30 may be configured to record impedance and/or other mapping data. Alternatively, the cryotreatment catheter 12 may include only one or more thermocouples 33 located distal to the one or more treatment elements 26, without an electrode. In any configuration, the cryotreatment catheter 12 may also include a thermocouple or other temperature sensor 33A within the treatment element 26. Further, the cryotreatment catheter 12 may include a reference electrode 34. The treatment element 26 may be a cryoballoon, as shown in FIGS. 1-3, and may also function as an occlusion element. The cryoballoon 26 may be coupled to the distal portion 22 of the elongate body 20 of the cryotreatment catheter 12. For example, the cryoballoon 26 may define a proximal portion or neck 36 that is affixed to or coupled to the distal portion 22 of the elongate body 20, and may further define a distal portion or neck 38 that is affixed to or coupled to the shaft 28 (such as the distal portion 40 of the shaft 28). The electrode 30 and/or one or more thermocouples 33 may be positioned just distal to the distal neck 38 of the cryoballoon 26. However, it will be understood that the cryoballoon 26 may be coupled, affixed, disposed on, integrated with, or otherwise attached to the elongate body 20 and/or the shaft 28. Additionally, multiple cryoballoons may be used, such as when the cryoballoon 26 is disposed within or without a second cryoballoon (not shown). The shaft 28 may lie along the longitudinal axis 32 and be longitudinally movable within the elongate body 20. In this manner, longitudinal movement of the shaft 28 will affect the shape of the cryoballoon 26. The proximal portion of the shaft 28 may be in mechanical communication with one or more steering mechanisms 41 in the handle 18 of the cryotreatment catheter 12, such that the shaft 28 may be longitudinally extended or retracted using one or more steering mechanisms 41, such as knobs, levers, wheels, pull cords, and the like. The shaft 28 may include a central lumen 42 and an opening in the distal end of the shaft for delivering fluid, such as the saline/contrast mixture, into the patient's body (for example, the pulmonary vein).

In addition to the shaft 28, the cryotreatment catheter 12 may include one or more lumens, such as a fluid injection lumen 43 and a fluid recovery lumen, for circulating coolant through from a fluid reservoir (which may be part of, disposed within, and/or in communication with the console 14) through the elongate body and to the cryoballoon 26, and for recovering expended coolant from the cryoballoon 26 and collecting the expended coolant within a fluid reservoir or venting to the atmosphere. Further, the cryotreatment catheter 12 may include a fluid delivery element 44 that is in fluid communication with the fluid injection lumen 43. As a non-limiting example, the fluid delivery element 44 may be wound about at least a portion of the shaft 28 within the cryoballoon 26, as shown in FIG. 1. The fluid delivery element 44 may be configured to direct a spray of coolant toward the distal portion of the cryoballoon 26. The fluid delivery element 44 may direct coolant in a direction that is substantially orthogonal (that is, approximately 90°) (as shown in FIG. 1) to the longitudinal axis 32 or in a direction that is at an angle that is less than 90° to the longitudinal axis 32. For example, the fluid delivery element 44 may include a plurality of outlet ports 45 that are configured to deliver fluid at an angle α from the longitudinal axis 32 of the device, such as at an angle α of between approximately 30° and approximately 45° (±5°) (as shown in FIG. 2). However, it will be understood that the fluid delivery element 44 may have any configuration that is suitable for directing fluid toward the distal portion of the cryoballoon 26. If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator (which may be part of, disposed within, and/or in communication with the console 14).

The mapping catheter 16 may be passable (longitudinally movable) through the shaft 28. The mapping catheter 16 may include one or more pairs of mapping elements 46, such as electrodes capable of sensing and recording electrograms from cardiac tissue. The one or more pairs of mapping elements 46 may be composed of metal or other electrically conductive material and may be affixed on an outer surface of the mapping catheter 16, integrated and flush with the body of the mapping catheter 16 (such that the mapping catheter has a smooth outer surface), may be areas of exposed electrically conductive material (for example, where an outer insulative layer has been removed), or may be otherwise affixed, coupled to, or integrated with the mapping catheter 16. The mapping catheter 16 may be in deformable and/or steerable using one or more steering mechanisms 41 into a variety of configurations. For example, the distal of the mapping catheter 16 may be deformable into a lasso-type configuration, such that the loop portion 48 and mapping elements 46 may be in contact with at least a portion of an inner circumference of a PV.

The console 14 may be in electrical and fluid communication with the cryotreatment catheter 12 and the mapping catheter 16, and may include one or more fluid (for example, cryotreatment coolant) reservoirs, including a saline/contrast reservoir 49, one or more coolant recovery and/or source reservoirs 50, energy generators 51, and computers 52 with displays 54, and may further include various other displays, screens, user input controls, keyboards, buttons, valves, conduits, connectors, power sources, processors, and computers for adjusting and monitoring system 10 parameters. The one or more coolant recovery and/or source reservoirs 50 may be in fluid communication with the cryoballoon 26 and the saline/contrast reservoir 49 may be in fluid communication with the central lumen 42 and distal opening 55 of the shaft 28. As used herein, the term "computer" may refer to any programmable data-processing unit, including a smart phone, dedicated internal circuitry, user control device, or the like. The computer 52 may include one or more processors 56 that are in electrical communication with the one or more pairs of mapping elements 46, the electrode 30, the one or more thermocouples 33, 33A, the one or more treatment elements 26, and/or one or more valves and programmable to execute an algorithm for locating one or more optimal treatment areas, for controlling the temperature of the one or more treatment elements 26, for generating one or more displays or alerts to notify the user of various system criteria or determinations, and/or for predicting temperature within target tissue based at least in part on signals from the electrode 30 and/or one or more other temperature sensors 33, 33A. As a non-limiting embodiment, the proximal portion of the mapping catheter 16 may include an electrical connection that is mateable to at least a portion of the console (for example, with the electrophysiology recording equipment) and in electrical communication with the one or more processors 56. Additionally, the electrode 30 may be in electrical communication with an energy generator 51 for the application of energy to the electrode 30 for thermally treating tissue. Furthermore, electrodes 30 and 34 may be used for 3D navigation of the catheter 12 within the atrial chamber and positioning the catheter 12 within, for example, a pulmonary vein. This may allow the operator to avoid placing the one or more treatment elements 26 too deep within the pulmonary vein, and may enable the operator to avoid extracardiac tissues and again navigate the one or more treatment elements 26 into the pulmonary vein if repeated ablation is needed. Additionally, marking the position of the one or more treatment elements 26 may allow the operator to mark the ablated pulmonary veins if multiple pulmonary vein branches and common ostium is present.

The console 14 may also include one or more valves that are in electrical and/or mechanical communication with, and controllable by, the console 14. For example, the computer 52 and/or one or more processors 56 may be programmable to control various system components, such as the one or more valves, to operate according to a duty cycle that includes opening and closing the one or more valves to regulate the flow of coolant through the system 10 and the catheter 12, and to thereby regulate the temperature of the treatment element 26 (for example, the cryoballoon 26). The duty cycle may be programmable by the user and/or may be automatically set by the console 14 according to a predicted tissue temperature based at least in part on signals from the electrode 30, mapping elements 46, and/or temperature sensors 33, 33A.

Referring now to FIG. 2, a close-up view of the distal portion of a first embodiment of the cryoballoon catheter is shown. As shown and described in FIG. 1, the cryotreatment catheter 12 may include a distal electrode 30. The cryotreatment catheter 12 may further include a reference electrode 34 and one or more thermocouples or other temperature sensors 33 if the electrode 30 is not configured to measure temperature. The electrodes 30, 34 may be composed of an electrically conductive material suitable for sensing temperature. As shown in FIGS. 1 and 2, the electrode 30 (and a thermocouple or temperature sensor 33, if included in the device) may be located distal to the cryoballoon 26. The electrode 30 may be coupled to, affixed to, disposed about, integrated with, or otherwise located on a distal portion of the cryotreatment catheter 12. The electrode 30 and/or one or more thermocouples 33 may be located immediately distal to the cryoballoon 26, such as on the shaft distal portion 40. For example, the electrode 30 may be adjacent to or abut the distal end of the cryoballoon 26. The reference electrode 34 may be located proximal to the cryoballoon 26, such as on the elongate body distal portion 22. As a non-limiting example, the cryoballoon 26 may have a diameter of approximately 23 mm to approximately 28 mm.

Referring now to FIG. 3, a cryotreatment catheter is shown positioned proximate a pulmonary vein ostium for a pulmonary vein ablation procedure (which may also be referred to as a pulmonary vein isolation (PVI) procedure). As used herein, the term "PV tissue" or "pulmonary vein tissue" may include tissue of the PV ostium, the PV antrum, LA wall tissue, and/or tissue at the junction between the LA and PV, and is not limited to tissue within the PV. In fact, ablation of tissue within the PV may be undesirable. The inflated cryoballoon 26 may be positioned at the pulmonary vein (PV) ostium to occlude the PV, or block the flow of blood from the PV into the left atrium (LA) of the heart. Occlusion of the PV not only serves to position the cryoballoon 26 to create a circumferential lesion around the PV ostium, but also prevents warm blood from flowing over the portions of the cryoballoon 26 that are in contact with the target tissue, thereby enhancing the ability of the cryoballoon 26 to reach sufficiently cold temperatures for creating permanent, and circumferential, cryoablation lesions on or in the target tissue. If the PV is not completely occluded, blood flow past the cryoballoon 26 may have the effect of raising the temperature of the cryoballoon 26, possibly resulting in the formation of reversible lesions on or in the target tissue. The blocked blood within the PV may be referred to as "stagnant" blood, whereas the blood within the LA may be referred to as "flowing" blood, as blood may still enter the LA from the other three PVs that are not being occluded by the catheter 12.

As shown in FIG. 3, the cryoballoon 26 may be positioned at the PV ostium such that the shaft distal portion 40, including the electrode 30 and/or one or more thermocouples 33, is disposed within the PV, within the stagnant blood. An injection of saline only or a mixture of saline and biocompatible contrast medium may be introduced into the PV at a fixed rate, volume, and temperature. For example, a volume (such as 8 mL) of saline (0.9%)/contrast mixture in an approximately 1:1 ratio (which includes less contrast medium than is used in current fluoroscopic imaging methods) may be transferred from the saline reservoir 49 to the central lumen 42 of the shaft 28, from where the saline may be expelled through the shaft distal opening and into the pulmonary vein. By the time the saline/contrast mixture is expelled, it may be chilled to a temperature of approximately 2-3° C. For example, the saline/contrast mixture may be chilled within the console 14 or within the system's fluid flow path before it is expelled from the central lumen 42. Further, the saline/contrast mixture may be expelled in an amount of approximately eight cc and at a pressure of approximately 125±12 PSI.

Continuous temperature measurements may be taken during device placement and cryoablation by the electrode 30 and the measurements may be used to determine whether the PV is completely occluded. For example, a slow increase in temperature within the PV following expulsion of the cooled saline/contrast mixture into the PV may indicate total PV occlusion, whereas a rapid temperature increase following expulsion of the cooled saline/contrast mixture may indicate poor PV occlusion. If temperature measurements indicate that the PV is not permanently ablated and/or less than fully occluded, the device may be repositioned until complete PV occlusion is indicated by evaluation of the temperature measurements. For example, the one or more processors 56 of the console computer 52 may be programmed to receive and process data from the one or more electrodes and/or thermocouples, and to generate an alert to the user indicating that the device should be repositioned to achieve complete PV occlusion or that the device is already optimally positioned.

In addition to temperature measurements, a visual evaluation may also be used to assess PV occlusion. For example, fluoroscopic imaging may be used to visually evaluation the time it takes for the saline/contrast mixture to dissipate from the area of the PV proximate the cryotreatment catheter 12. Further, visual evaluation may be used in addition to temperature measurements. Generally, if the PV is completely occluded by the treatment element 26, it will take longer for the saline/contrast mixture (which may appear as being darker than the surrounding blood under fluoroscopic imaging) to dissipate from the area proximate the cryotreatment catheter 12. In contrast, if PV occlusion is poor, the saline/contrast mixture may quickly dissipate with the normal direction of blood flow, such as from the pulmonary vein into the left atrium of the heart. The time it takes the saline/contrast mixture to dissipate vs. the time it takes the chilled saline/contrast to increase from the injection temperature to a threshold temperature may be compared to evaluate PV occlusion. For example, the saline/contrast may be injected at approximately 2-3° C., and the time it takes for the cooled saline/contrast to reach a threshold temperature of approximately 38° C. (that is, the rate of temperature increase following injection, or DT/dt) may be calculated. The temperature of the saline/contrast may be first measured at approximately 1-2 seconds after injection, and may be measured repeatedly at additional time intervals until the temperature reaches approximately 38° C. A non-limiting comparison is shown below:

TABLE 1

Comparison between time to saline/contrast dissipation from injection (sec) and time to recover from approximately 2-3° C. to approximately 38° C.

|  | Time to saline/contrast dissipation from injection (sec) | Time to recover from approx. 2-3° C. to approx. 38° C. (sec) |  |
| --- | --- | --- | --- |
| Good occlusion | 37.6 ± 18.4 | 75.4 ± 48.7 | N = 14, p < 0.01 |
| Fair occlusion | 19.0 ± 8.2 | 34.4 ± 18.6 | N = 18, p < 0.01 |
| Poor occlusion | 5.8 ± 3.3 | 20.8 ± 13.4 | N = 13, p < 0.01 |

After PV occlusion assessment, which may be conducted prior to thermally treating target tissue, the cryoballoon 26 may then be cooled to a temperature sufficient to ablate tissue and applied to the tissue surrounding the PV opening (for example, the PV ostium and/or the PV antrum). Once the cryoballoon 26 has reached ablation temperature, the temperature sensed by the electrode 30 or the thermocouple positioned distal to the cryoballoon 26 and within the PV and a temperature sensed within the cryoballoon may be compared for each of the occlusion ratings (i.e. good occlusion, fair occlusion, and poor occlusion). The thermocouple or other temperature sensor 33A may be located within the cryoballoon 26. The comparison shown in Table 2 may follow the trend of the comparison shown in Table 1. However, since the temperatures sensed within the cryoballoon 26 during ablation may not be significantly different depending on the quality of occlusion, the comparison between temperature sensed by the distal electrode 30 or the one or more distal thermocouples 33 and the time to recovery to approximately 38° C. may be more informative to an operator than the comparison shown in Table 2. During experimentation, the PV was cryoablated at each of the occlusion conditions (good, fair, poor) and the temperature recorded at the electrode 30 and/or the one or more distal thermocouples 33 vs. the temperature recorded by the thermocouple 33A within the cryoballoon 26 was compared, which is shown in Table 2 below:

TABLE 2

Temperature sensed by distal electrode 30 compared to temperature sensed within cryoballoon.

|  | Temperature sensed by electrode 30 (° C.) | Temperature sensed within cryoballoon 26 (° C.) |  |
| --- | --- | --- | --- |
| Good occlusion | −3.4 ± 18.0 | −58.0 ± 7.7 | N = 9, p < 0.01 |
| Fair occlusion | 6.2 ± 17.5 | −51.72 ± 9.0 | N = 11, p < 0.01 |
| Poor occlusion | 23.3 ± 11.5 | −41.7 ± 4.8 | N = 5, p < 0.01 |

Electrical isolation of the PV, or the destruction of aberrant electrical currents originating within the PV, may be achieved when the cryoballoon 26 is completely occluding the PV (an indication of good occlusion is determined). PV isolation may be determined based on data received by the console 14 from the mapping catheter 16. Thus, in practice, the cryoballoon 26 may be cooled to a temperature sufficient to ablate tissue and applied to the tissue surrounding the PV opening when good occlusion is communicated by the system 10 to the user.

Figure 4A:
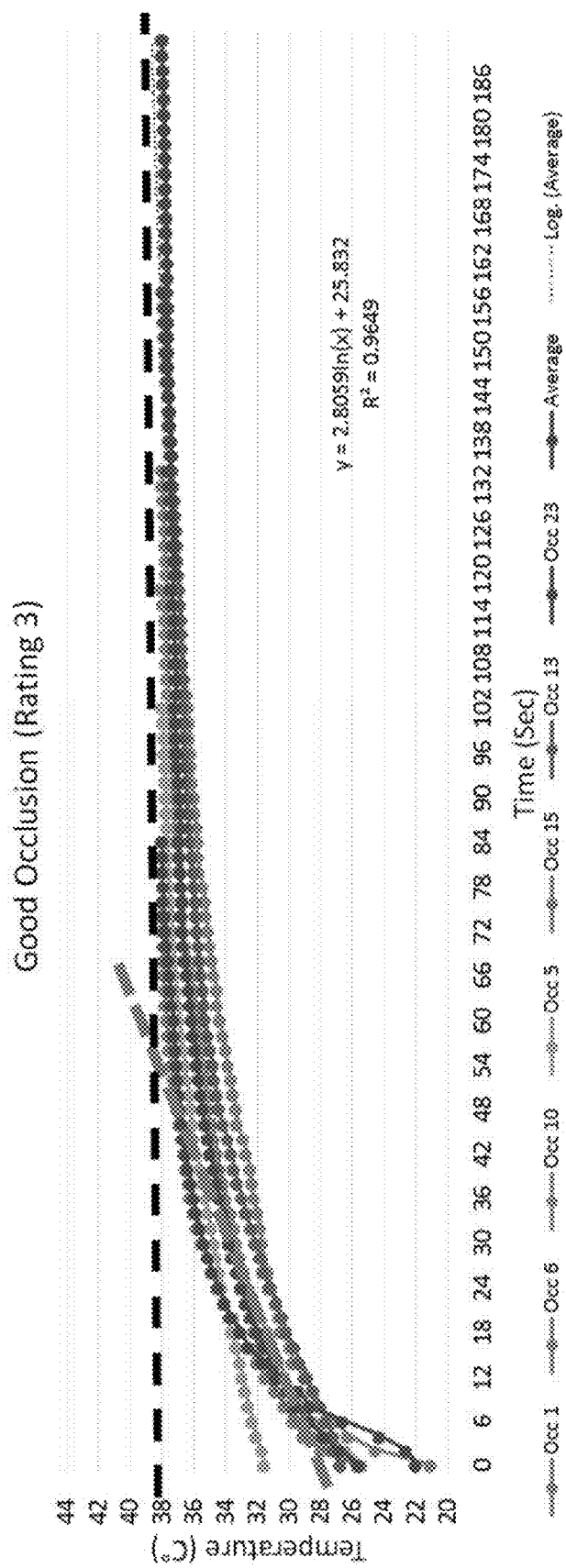
FIGS. 4A-4D show exemplary charts of data for the assessment of pulmonary vein occlusion based on temperature.
Figure 4B:
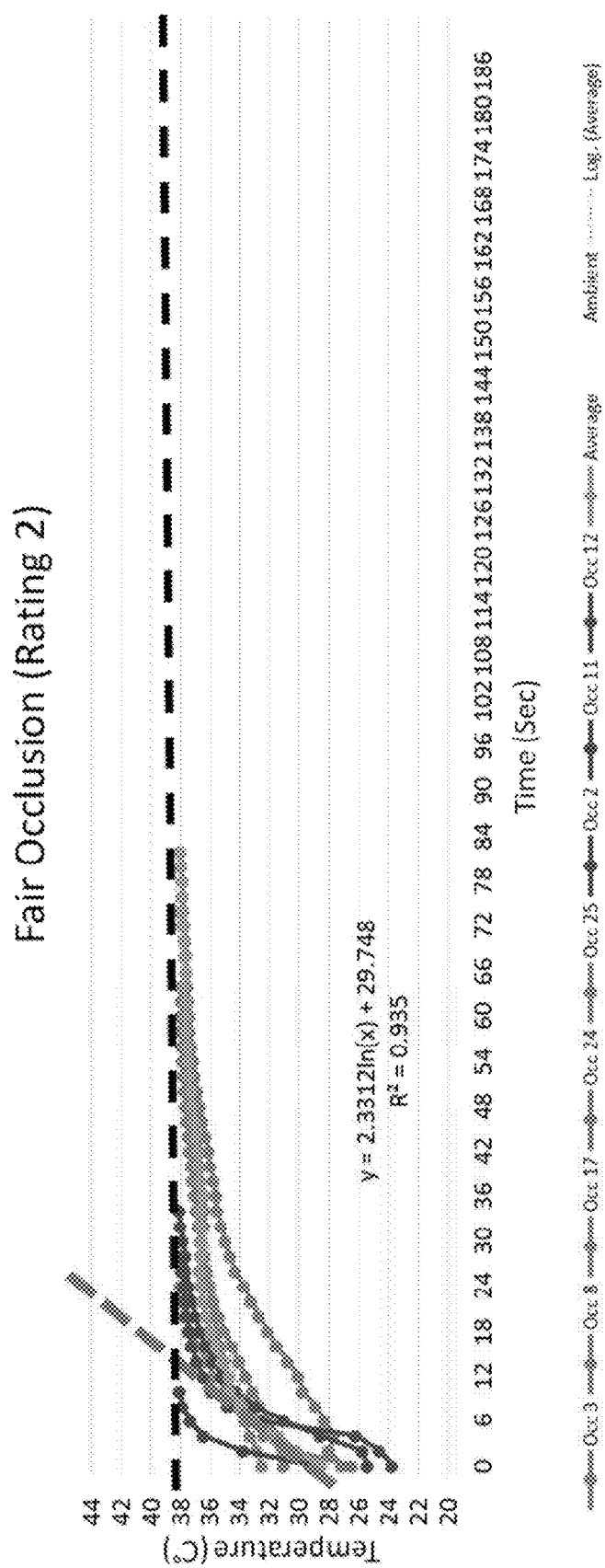
Figure 4C:
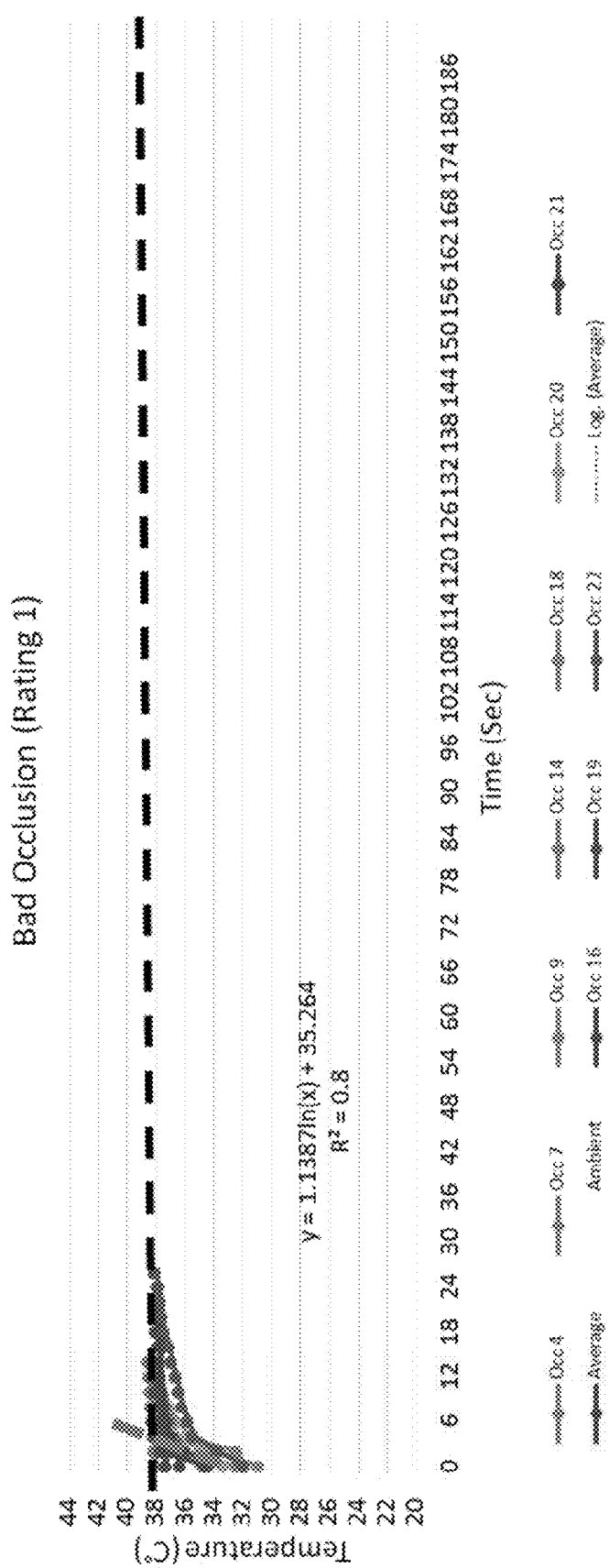
Figure 4D:
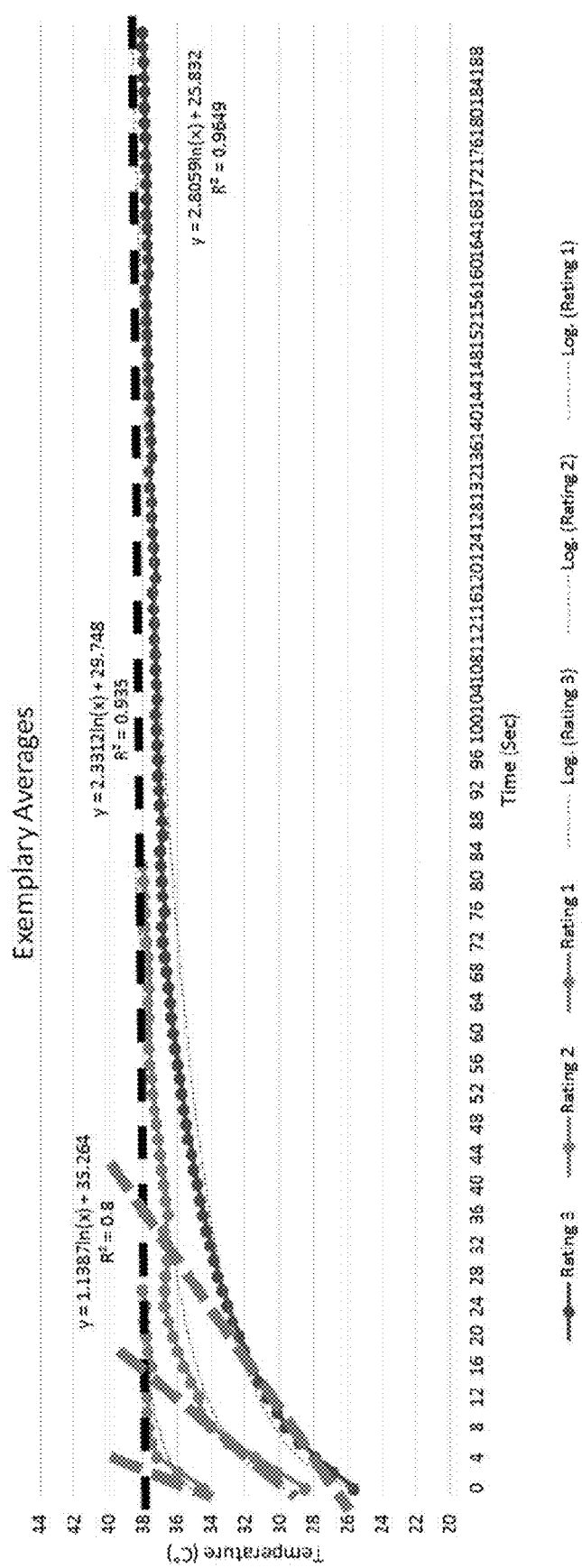

Referring now to FIGS. 4A-4D, exemplary charts of data for the assessment of pulmonary vein occlusion are shown. FIGS. 4A-4D show assessment of PV occlusion based on temperature sensed by the distal electrode 30 (or one or more distal thermocouples 33). If good occlusion quality is indicated, a high-quality lesion may be predicted. A high-quality lesion may be one that is circumferential about the pulmonary vein ostium and/or that is a permanent lesion. Generally, the saline/contrast mixture may be expelled from the distal end of the shaft 28 into the pulmonary vein, against the normal direction of blood flow, which may cause the expelled saline/contrast mixture to flow back toward the device and over the distal electrode 30 and/or distal thermocouples 33. The quality of occlusion may affect the temperature of the saline/contrast mixture as it passes the distal electrode 30 and/or distal thermocouples 33. FIG. 4A shows temperature curves over time for eight discrete tests and an average temperature curve over time for an occlusion that is considered to be a good occlusion (slow temperature recovery). FIG. 4B shows temperature curves over time for eight discrete tests and an average temperature curve over time for an occlusion that is considered to be a fair occlusion (more rapid temperature recovery than that shown in FIG. 4A). FIG. 4C shows temperature curves over time for eleven discrete tests and an average temperature curve over time for an occlusion that is considered to be a poor occlusion (most rapid temperature recovery of those shown in FIGS. 4A, 4B, and 4C). FIG. 4D shows exemplary average temperature curves over time for each of occlusions that are considered to be good, fair and poor occlusions. As is shown in FIGS. 4A-4D (and as is discussed above), with good occlusion, the time for the temperature to recover to approximately 38° C. is longer than when the occlusion is either qualified as fair or poor. That is, the rate of temperature increase with good occlusion is less than the rate of temperature increase with fair or poor occlusion.

To obtain the data of FIGS. 4A-4D, the cryoballoon 26 may be placed proximate a pulmonary vein ostium, such that the pulmonary vein is believed to be occluded. Then, temperature sensed by the distal electrode 30 (or distal thermocouple 33) and the time to recover from approximately 2-3° C. to approximately 38° C. can be recorded and used to evaluate the quality of occlusion, with a longer recovery time indicating good occlusion. Additionally or alternatively, the rate of temperature increase may be used to evaluate quality of occlusion over a period of between approximately 2 and approximately 15 seconds, with a lower rate of temperature increase indicating good occlusion. Using this data, the occlusion can be qualified as good, fair, or poor. The one or more processors 56 may receive and process data from the cryotreatment catheter 12 and the mapping device 16, and may communicate the results, such as occlusion assessment determinations, to the user via the one or more displays 54. Additionally or alternatively, the system 10 may communicate results to the user via one or more visual or audio alerts. Occlusion assessment determinations may be displayed to the user graphically in a manner that is quickly understood. As a non-limiting example, a colored graphical element may be displayed, with the color green indicating good PV occlusion, the color yellow indicating fair PV occlusion, and the color red indicating poor PV occlusion.

In practice, the data shown and discussed herein may be used to assess pulmonary vein occlusion quality in a patient using only the cooled saline without the contrast medium. Although use of the saline/contrast mixture may be useful for visual assessment of pulmonary vein occlusion quality during testing, it may be desirable to use temperature data alone without exposing the patient to contrast medium. Therefore, although the cooled fluid is referred to herein as "saline/contrast mixture," it will be understood that saline only may be expelled into the pulmonary vein to assess occlusion.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for predicting lesion quality, the system comprising:
   a treatment device, the treatment device including at least one temperature sensor; and
   a console including:
      a source of cooled saline in fluid communication with the treatment device, the cooled saline being injected from the treatment device;
      an energy generator in electrical communication with the treatment device; and
      a processor, the at least one temperature sensor being configured to send temperature data to the processor, the processor being programmed to receive temperature data recorded by the treatment device and to calculate a rate of temperature increase in the cooled saline after injection from the treatment device, the processor being further programmed to determine a pulmonary vein occlusion status based at least in part on the rate of temperature increase, the lesion quality being based at least in part on the pulmonary vein occlusion status.

2. The system of claim 1, wherein cooled saline is injected from the treatment device at an injection temperature, the processor being programmed to calculate a rate of temperature increase from the injection temperature to a threshold temperature after injection of the cooled saline from the treatment device.

3. The system of claim 2, wherein the threshold temperature is 38° C.

4. The system of claim 2, wherein the injection temperature is 2° C. to 3° C.

5. The system of claim 1, wherein a determination that the pulmonary vein is partially occluded includes at least one of assigning the occlusion status by the processor a poor rating and assigning the occlusion status a fair rating and a determination that the pulmonary vein is completely occluded includes assigning the occlusion status by the processor a good rating.

6. The system of claim 5, wherein occlusion status is assigned a good rating when the rate of temperature increase has a first value, occlusion status is assigned a fair rating when the rate of temperature increase has a second value, and occlusion status is assigned a poor rating when the rate of temperature increase has a third value, the first value being less than each of the second value and the third value.

7. The system of claim 1, wherein the treatment device includes a cryoballoon and a thermocouple located distal to the cryoballoon.

8. The system of claim 7, wherein the treatment device includes an electrode located distal to the cryoballoon, the thermocouple being integrated with the electrode.

9. The system of claim 7, wherein the treatment device further includes an electrode proximate the thermocouple.

10. The system of claim 7, wherein the treatment device further includes a shaft having a central lumen and a distal opening, the shaft being at least partially disposed within the cryoballoon, the central lumen and distal opening being in fluid communication with the source of cooled saline.

11. The system of claim 1, wherein the cooled saline includes a volume of radiopaque contrast medium and the cooled saline with contrast medium is injected into a pulmonary vein.

12. The system of claim 11, wherein the processor is further programmed to calculate a dissipation time it takes the cooled saline with contrast medium to dissipate within the pulmonary vein, the processor being further programmed to determine the pulmonary vein occlusion status based at least in part on the dissipation time.

13. The system of claim 12, wherein occlusion status is assigned a good rating when the dissipation time has a first value, occlusion status is assigned a fair rating when the dissipation time has a second value, and occlusion status is assigned a poor rating when the dissipation time has a third value, the first value being less than each of the second value and the third value.

14. The system of claim 2, wherein the processor is further programmed to calculate a rate of temperature increase in the cooled saline from the injection temperature over a threshold period of time.

15. The system of claim 14, wherein the threshold period of time is between 2 and 15 seconds.

16. The system of claim 1, wherein the cooled saline is injected from the treatment device at an injection temperature, the processor being programmed to calculate a rate of temperature increase from the injection temperature to a temperature at two seconds after injection of the cooled saline from the treatment device.

17. A system for predicting lesion quality, the system comprising:
  a treatment device including an occlusion element and a thermocouple distal to the occlusion element, the treatment device injecting cooled saline into a pulmonary vein at an injection temperature of between 2° C. and 3° C.; and
  a processor in communication with and receiving temperature data from the thermocouple, the processor programmed to:
    calculate a rate of temperature increase from the cooled saline from the injection temperature to a temperature of 38° C. over a predetermined period of time after the cooled saline is injected from the treatment device; and
    determine a pulmonary vein occlusion status based at least in part on the rate of temperature increase, the lesion quality being based at least in part on the pulmonary vein occlusion status.

18. The system of claim 17, wherein an occlusion status of good is assigned when the rate of temperature increase has a first value, an occlusion status of fair is assigned when the rate of temperature increase has a second value, and an occlusion status of poor is assigned when the rate of temperature increase has a third value, the first value being less than each of the second value and the third value.

19. The system of claim 18, wherein the lesion quality is assigned a value of good when the occlusion status is good.

20. A method for predicting lesion quality, the method including:
  injecting cooled saline from a medical device into a pulmonary vein, the medical device including an occlusion element at least partially occluding the pulmonary vein and a distal thermocouple positioned within the pulmonary vein;
  recording a temperature by the thermocouple within the pulmonary vein at each of a plurality of time intervals after injection of the cooled saline;
  comparing, with a processor of a console that is in communication with the medical device, the temperatures recorded at each of the plurality of time intervals;
  assessing, with the processor of the console, the quality of an occlusion of the pulmonary vein by the medical device based on the comparisons; and at least one of:
    repositioning the medical device when the quality of the occlusion is determined to be one of fair and poor; and
    ablating tissue surrounding the pulmonary vein with the occlusion element when the quality of the occlusion is determined to be good.

21. The method of claim 20, wherein comparing the temperatures recorded at each of the plurality of time intervals includes determining a recovery time it takes the temperature within the pulmonary vein to increase from between 2° C. and 3° C. to 38° C.

22. The method of claim 21, wherein the quality of occlusion is determined to be good when the recovery time is 75.4±48.7 seconds.

* * * * *